(12) United States Patent
McManus et al.

(10) Patent No.: US 12,411,118 B2
(45) Date of Patent: Sep. 9, 2025

(54) MICRO-ENVIRONMENT APPARATUS AND METHOD FOR AIR SENSOR

(71) Applicant: Grand Valley State University, Allendale, MI (US)

(72) Inventors: Sean M. McManus, Allendale, MI (US); Leo M. McCormick, Grand Rapids, MI (US); Tom Michalak, Irons, MI (US)

(73) Assignee: Grand Valley State University, Allendale, MI (US)

( * ) Notice: Subject to any disclaimer, the term of this patent is extended or adjusted under 35 U.S.C. 154(b) by 1096 days.

(21) Appl. No.: 17/240,291

(22) Filed: Apr. 26, 2021

(65) Prior Publication Data

US 2021/0333254 A1 Oct. 28, 2021

Related U.S. Application Data

(60) Provisional application No. 63/016,023, filed on Apr. 27, 2020.

(51) Int. Cl.
*G01N 33/00* (2006.01)

(52) U.S. Cl.
CPC ....... *G01N 33/007* (2013.01); *G01N 33/0026* (2013.01); *G01N 33/0073* (2013.01); *G01N 33/0072* (2024.05)

(58) Field of Classification Search
CPC ....... G01N 2033/0072; G01N 33/0026; G01N 33/007; G01N 33/0073; G01N 15/00; G01N 21/3504; G01N 21/783; G01N 25/46; G01N 25/488; G01N 2027/222; G01N 27/223; G01N 27/407; G01N 27/4114; G01N 27/404; G01N 27/4162; G01N 31/223; G01N 31/221; G01N 31/222; G01N 31/224; G01N 33/0004; G01N 33/497; Y02B 30/70
See application file for complete search history.

(56) References Cited

U.S. PATENT DOCUMENTS

| | | |
|---|---|---|
| 5,184,501 A | 2/1993 | Lewis et al. |
| 5,292,280 A | 3/1994 | Janu et al. |
| 5,293,771 A | 3/1994 | Ridenour |
| 5,357,781 A | 10/1994 | Tikijian |

(Continued)

FOREIGN PATENT DOCUMENTS

CN 201589957 U * 9/2010

*Primary Examiner* — John E Breene
*Assistant Examiner* — Truong D Phan
(74) *Attorney, Agent, or Firm* — Price Heneveld LLP

(57) ABSTRACT

A remote test apparatus is configured to simulate an environment of at least one remotely located room and configured to receive at least one air sample from the at least one remotely located room. The apparatus includes a sealed enclosure forming an interior cavity and including an inlet in connection with the at least one remotely located room and an outlet in connection with a sample collection unit. The sample collection unit is configured to communicate the at least one air sample from the remotely located room at a first flow rate. The apparatus further includes at least one sensor disposed in the interior cavity and at least one air transfer unit configured to transfer test air from the interior cavity of the sealed enclosure to the at least one sensor at a second flow rate.

19 Claims, 8 Drawing Sheets

(56) References Cited

U.S. PATENT DOCUMENTS

| | | | |
|---|---|---|---|
| 5,394,934 | A | 3/1995 | Rein et al. |
| 5,464,369 | A | 11/1995 | Federspiel |
| 5,550,752 | A | 8/1996 | Federspiel |
| 5,976,010 | A | 11/1999 | Reese et al. |
| 6,125,710 | A | 10/2000 | Sharp |
| 6,241,950 | B1 | 6/2001 | Veelenturf et al. |
| 6,425,297 | B1 | 7/2002 | Sharp |
| 7,302,313 | B2 | 11/2007 | Sharp et al. |
| 7,389,158 | B2 | 6/2008 | Desrochers et al. |
| 7,434,413 | B2 | 10/2008 | Wruck |
| 8,066,558 | B2 | 11/2011 | Thomle et al. |
| 8,147,302 | B2 | 4/2012 | Desrochers et al. |
| 9,109,981 | B2 | 8/2015 | Sharp |
| 2013/0260668 | A1 | 10/2013 | Stakutis et al. |
| 2015/0253165 | A1 | 9/2015 | Ajay et al. |
| 2015/0323427 | A1 | 11/2015 | Sharp |
| 2017/0158020 | A1* | 6/2017 | Park .................... G01N 21/534 |
| 2018/0363939 | A1* | 12/2018 | McCormick ............. G01N 1/24 |
| 2020/0264155 | A1* | 8/2020 | Alves Fortunato .... G01N 33/22 |

* cited by examiner

MICRO-ENVIRONMENT APPARATUS AND METHOD FOR AIR SENSOR

CROSS-REFERENCE TO RELATED APPLICATIONS

This application claims priority under 35 U.S.C. § 119(e) and the benefit of U.S. Provisional Application No. 63/016,023 entitled MICRO-ENVIRONMENT APPARATUS AND METHOD FOR AIR SENSOR, filed on Apr. 27, 2020, by McManus et al., the entire disclosure of which is incorporated herein by reference.

TECHNOLOGICAL FIELD

The present disclosure generally relates to air monitoring systems and, more particularly, relates to air monitoring systems utilizing multipoint air sampling.

BACKGROUND OF THE DISCLOSURE

Building air supply and control systems are becoming increasingly important due to increases in energy cost. In various building ventilation systems (e.g. HVAC systems), it may be beneficial to improve data acquisition for each room of the building. The disclosure provides for a variety of improvements in air sampling and air quality control for building ventilation and control systems.

BRIEF SUMMARY

According to one aspect of the present disclosure, a remote test apparatus is configured to simulate an environmental condition of at least one remotely located room. In operation, the apparatus is configured to receive at least one air sample from the at least one remotely located room. The apparatus comprises a sealed enclosure forming an interior cavity and comprising an inlet in connection with the at least one remotely located room and an outlet in connection with a sample collection unit. The sample collection unit is configured to draw the at least one air sample from the remotely located room at a first flow rate. The apparatus further comprises at least one sensor disposed in the interior cavity and at least one air transfer unit configured to transfer test air from the interior cavity of the sealed enclosure to the at least one sensor at a second flow rate.

According to another aspect of the disclosure, a method for simulating an environmental condition of at least one remotely located room is disclosed. The method includes supplying at least one air sample at a first flow rate from the at least one remotely located room to an interior cavity of a sealed enclosure. The method further includes sampling the at least one air sample within the interior cavity at a second flow rate different than the first flow rate and detecting the environmental condition in the at least one air sample at the second flow rate within the interior cavity. A test environment within the interior cavity simulates the environmental condition of the remotely located room.

In yet another aspect of the disclosure, a remote test apparatus is configured to simulate an environment of at least one remotely located room and configured to receive at least one air sample from the at least one remotely located room. The apparatus includes a sealed enclosure forming an interior cavity formed by a sealed boundary wall. The sealed enclosure includes an inlet in connection with the at least one remotely located room and an outlet in connection with a sample collection unit. The sample collection unit is configured to transfer the at least one air sample from the remotely located room at a first flow rate. The test apparatus also includes at least one sensor disposed in the interior cavity and a pressure sensor that detects a pressure differential between the interior cavity and a local environment proximate the sealed enclosure. A controller is configured to detect a system error in response to changes in the pressure differential.

These and other aspects, objects, and features of the present disclosure will be understood and appreciated by those skilled in the art upon studying the following specification, claims, and appended drawings. It will also be understood that features of each embodiment disclosed herein may be used in conjunction with, or as a replacement for, features of the other embodiments.

DETAILED DESCRIPTION OF EMBODIMENTS

Figure 1:
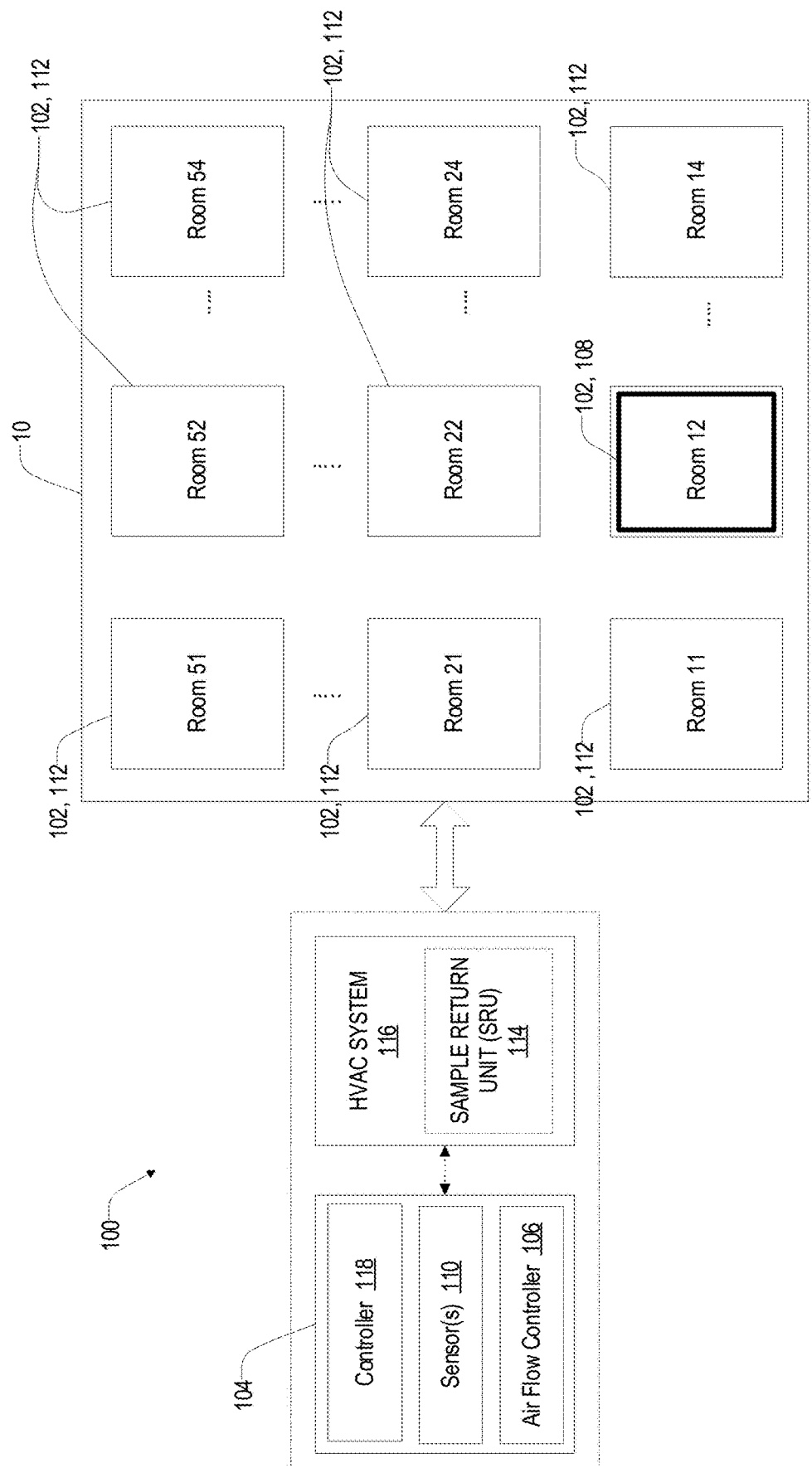
FIG. 1 is a block diagram of a building demonstrating a plurality of rooms incorporating an air sampling system.

The present illustrated embodiments reside primarily in combinations of method steps and apparatus components related to an air monitoring device. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Modern heating, ventilation, and air conditioning (HVAC) systems may provide for independent control of various regions or rooms within a building. In this way, climate control and air quality may be monitored and controlled for each region or room. In addition to the benefits of improved comfort and air quality, systems may also be configured to reduce energy consumption. In some cases, conserving energy may include determining occupancy of each room or region. In response to the occupancy or level of occupancy, the HVAC setting may be optimized to ensure that the air quality is maintained. However, there are a variety of challenges that may be associated with implementing such systems on a large scale while maintaining economical HVAC control solutions. The following detailed description provides for a system and control method for an air sampling system that is both effective and economical.

Figure 2:
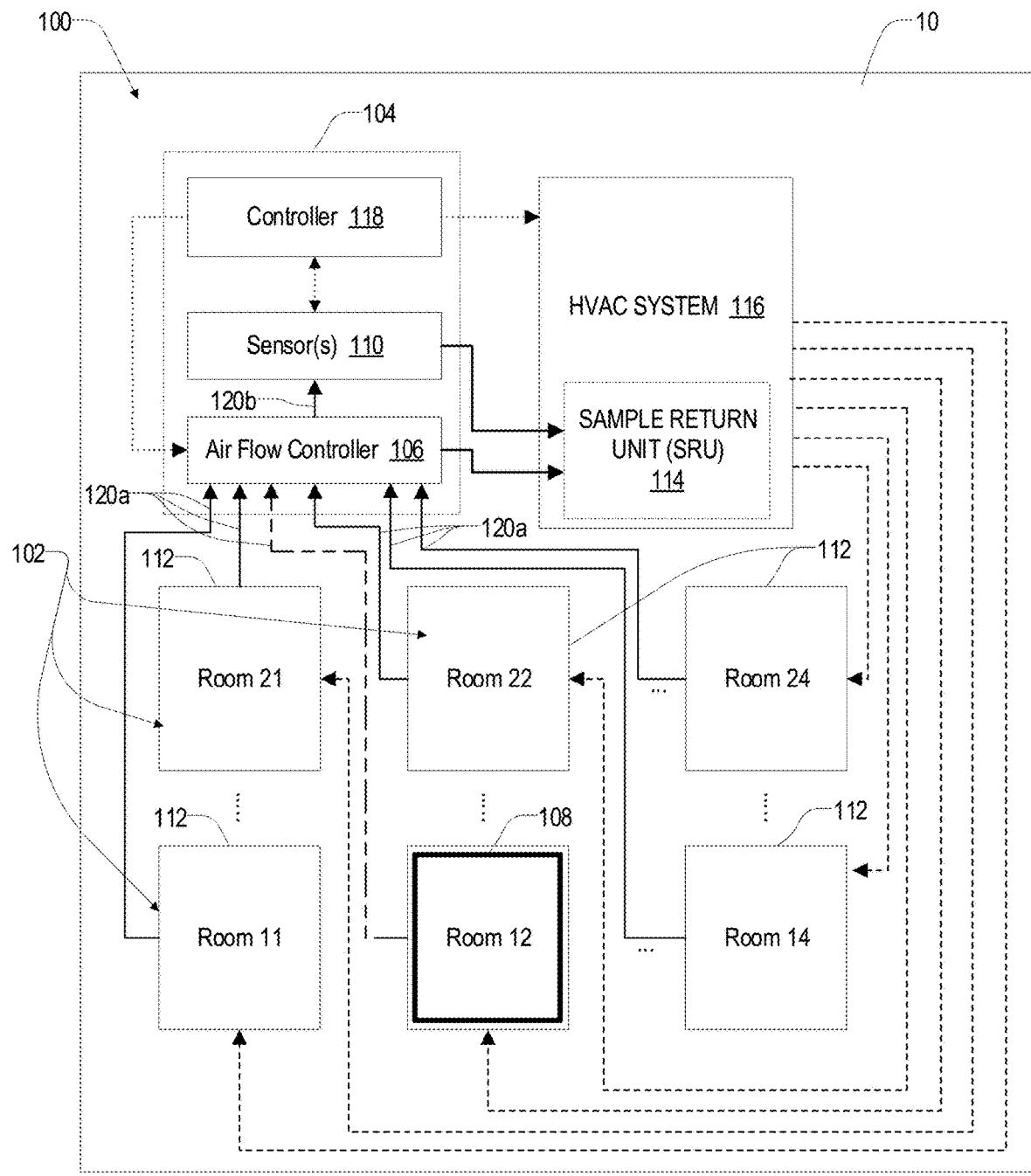
FIG. 2 is a block diagram of a building having an air sampling system.

Referring to FIGS. 1 and 2, block diagrams of a building 10 having an air sampling system 100 is shown. The air sampling system 100 may be configured to selectively measure at least one air quality characteristic from a plurality of areas of the building 10. For example, the system 100 may be configured to monitor various volumetric regions of a single room and/or monitor the conditions of each of a plurality of rooms 102 (e.g. rooms 11-14, 21-24, 51-54, etc.). The plurality of rooms 102 or areas of the building 10 may correspond to regions or volumetric spaces within a commercial building, residential building, multipurpose building, etc. The disclosure may provide for various novel aspects configured to limit the installation and operating cost of the system 100, and may also provide for improved operational performance.

In an exemplary embodiment, the system 100 may comprise an air sampling device 104. The air sampling device 104 may correspond to a scalable monitoring device configured to sample the air from each of the plurality of rooms 102 via an air flow controller 106. The air flow controller 106 may comprise a header configured to receive multiple inputs corresponding to each of the plurality of rooms 102. The air flow controller 106 may be configured to selectively direct a room air sample from a selected room 108 (e.g. room 12) to one or more sensors 110. While drawing the room air sample from the selected room 108, the air sampling device 104 may be configured to draw air or communicate air from the idle rooms 112 of the plurality of rooms 102. In this configuration, the sampling device may be operable to monitor a condition of the air in each of the plurality of rooms 102 with only limited and consistent delay to gather a current air sample. As will be discussed further herein, the delay of the air sampling device 104 to update a sample for each selected room may be consistent regardless of a distance of the selected room 108 from the sensor 110 of the sampling device 104.

The system 100 may further comprise an air transport motivator or sample return unit 114. The sample return unit 114 may correspond to an energy efficient air transport unit configured to function without a need for direct electrical power. In such embodiments, the sample return unit 114 may be configured to generate suction to draw the room air samples from each of the plurality of rooms 102 via a bulk supply fan of an existing heating, ventilation, and air conditioning (HVAC) system 116 of the building 10. For example, the sample return unit 114 may correspond to a Venturi vacuum device configured to utilize differential pressure derived from the bulk supply fan of the HVAC system 116. Further details of the sample return unit 114 are discussed in reference to FIG. 3. The HVAC system 116 may be configured to provide heating, ventilation, and air conditioning to each of the rooms 102. In this configuration, the sampling return unit 114 may be configured to function without a direct supply of electrical energy.

Though the sample return unit 114 is described in the exemplary embodiment as a Venturi vacuum device, in some embodiments, the sample return unit 114 may recover the room air samples utilizing conventional vacuum pumps or fans. For example, in some embodiments, the sample return unit 114 may utilize suction created via a reciprocating pump, screw or turbine compressor, or various devices configured to displace air in response to receiving electrical current. Such devices may be utilized to provide vacuum pressure to return the room air samples. However, these devices may be noisy, inefficient, and require more maintenance than the Venturi vacuum device disclosed herein.

In the exemplary embodiment utilizing the Venturi vacuum device, the only energy usage of the sample return unit 114 may be a small parasitic energy drawn from the bulk supply fan of the HVAC system 116. For example, the bulk supply fan may consume a small and potentially negligible increased power due to the energy usage of the sample return unit 114. The change in power usage may particularly be negligible when the air sampling system 100 is implemented in large buildings having multiple rooms and high volume HVAC systems 116. In this way, the air sampling system 100 may improve efficiency while limiting components and related maintenance that may be required when utilizing active devices to provide vacuum pressure to return the room air samples. As disclosed, the sample return unit 114 may utilize the existing fluid pressure from the HVAC system 116 to power the sample return unit 114 via the Venturi effect to improve efficiency and limit maintenance.

In operation, the sample return unit 114 may draw room air samples from each of the plurality of rooms 102 perpetually during operation of the bulk supply fan of the HVAC system 116. For example, the controller 118 of the air sampling system 100 may be configured to control the air flow controller 106 to direct a room air sample of a selected room 108 to a quality sensor of the at least one sensor 110 to measure a condition or quality parameter of the selected room 108. The air quality sensor is identified as element 140 in FIG. 3 and is discussed further in reference to FIG. 3. Additionally, the air flow controller 106 may be configured to retrieve and purge room air samples 132 from each of the idle rooms 112 (e.g. rooms 11, 13, 14, 21-24, 51-54, etc.).

By continuously drawing the room air samples from each of the idle rooms 112 and the selected room 108, the air sampling system 100 may continuously supply updated air samples to the air flow controller 106. In this way, the system 100 may supply air samples from each of the rooms 102 to a central location of the air flow controller 106 and selectively direct the air sample from the selected room 108 to the air quality sensor 140. Accordingly, the system 100 may avoid delays in updating the air samples from each of the idle rooms 112 that may otherwise be required to purge an associated length of each of the supply lines 120 or more specifically, each of a plurality of room air sample supply lines 120a from each of the rooms 102 to the air flow controller 106. By continuously supplying updated air samples from each of the rooms 102 containing air that is representative of a current air quality, the sampling system 100 is operable to test each of the rooms 102 without significant delay that may otherwise be required to purge air samples. Accordingly, the air supplied from the air flow controller 106 to the at least one sensor 110 may only need to be purged from the air in the sensor supply line 120b rather than each of the air sample supply lines 120a when changing the selected room 108 among the plurality of rooms 102.

In operation, the controller 118 may measure the air quality of one or more of the rooms 102 by cycling the selected room 108 to supply an air sample from one or more of the rooms 102. For example, during such an operation, the controller 118 may control the air flow controller 106 and the at least one sensor 110 to measure the air quality of room 12. Following the measurement of the air quality in room 12, the controller 118 may generate a control signal configured to change the air flow controller 106 to select room 22 as the selected room 108. In this configuration, the idle rooms 112 may include rooms 11-14, 21, 23, 24, 51-54; the air samples from these rooms may be purged while the selected room 108 is designated as room 22.

The room air sample from room 22 may be directed by the air flow controller 106, such that the air entering the at least one sensor 110 is from room 22. The controller 118 may then allow a predetermined period of time for the room air sample from room 12 to purge from a sensor supply line 120b and to allow time for a change in the sampled air to become stable in the sensor 110. Once the predetermined period of time has lapsed, the controller 118 may monitor the at least one sensor 110 to identify a condition or quality parameter of the room air sample for room 22. If the room air samples from each of the rooms 102 were not delivered to the air flow controller 106 throughout operation, the purge time may increase dramatically and vary for each of the rooms 102 due to variations in the lengths of the air sample supply lines 120a. Such variations and increases in purge time may result in delayed correction of air quality in each of the rooms 102 as well as increased maintenance and operational cost for the sampling system 100.

The controller 118 of the air sampling system 100 may continue to control the air flow controller 106 to test the condition or an air quality parameter of each of the rooms 102 in any sequence. The controller 118 may be configured to monitor each of the room air samples for each of the rooms 102 for a monitoring period, which may be independently specified for one or more of the rooms 102. Additionally, the air sampling system 100 may be configured to monitor the rooms 102 sequentially or in any order. For example, the controller 118 may be configured to control the air flow controller 106 to monitor a frequently occupied room with a greater frequency than other rooms of the plurality of rooms 102.

As discussed previously, the continuous delivery of the room air samples for each of the rooms 102 by the air flow controller 106 may limit a purging time required to gather a current or updated sample from the selected room 108. Additionally, the continuous delivery of the room air samples may limit a flow rate necessary for the sample return unit 114. In this way, the air sampling system 100 can maintain a low cycle time allowing the controller 118 to monitor the condition or an air quality parameter of each of the rooms 102 over a limited cycle time. The cycle time may correspond to a time required for the controller 118 to measure the condition or an air quality parameter of each of the rooms 102 and may also be referred to as a refresh rate.

As further discussed in reference to FIGS. 5, 6, 7, and 8; in some implementations, the system 100 may comprise a remote test environment 122, which may utilize a sealed enclosure 124 to create a micro-environment 126 for each of the selected rooms 108. The remote test environment 122 may be formed within the sealed enclosure 124, which may be housed within the sampling device 104. In operation, the air flow controller 106 may continuously cycle sampled air from each of the rooms 102 and selectively deliver the air from the selected room 108 into the sealed enclosure 124 such that the micro-environment 126 is generated within an interior cavity 128 of the sealed enclosure 124. In this way, the system 100 may provide for a simulated environment with representative air quality conditions to that of the selected room 108 and each of the rooms 102 in a remote location separate from each of the rooms 102 within the sampling device 104.

Within the remote test environment 122 formed by the sealed enclosure 124, at least one of the sensors 110 may be housed such that the air flow controlled by the air flow controller 106 may be delivered from the selected room 108 into the interior cavity 128. In this way, the system may generate similar air conditions to those of the selected room 108 within the sealed enclosure 124, such that the one or more sensors 110 disposed therein may be operable to sample and test the micro-environment 126 and thereby simulate a test of the ambient air conditions within the selected room 108. The operation of the remote test environment 122 may be cycled for each of the rooms 102 in connection with the sampling device 104 without appreciable lag or delay as a result of the continuous delivery of the room air samples from each of the rooms 102. In this way, the system 100 may provide for advanced testing of simulated ambient air conditions in each of the rooms 102 while only requiring a limited vacuum pressure and corresponding flow rate of the room air samples supplied to the sampling device 104 by the flow controller 106.

Systems that do not utilize continuous delivery of the room air samples may require a significant increase in cycle time to monitor the rooms 102 or an increased flow rate for an air sample return unit. For example, the cycle time may increase due to increased purge time required to receive air sample data representative of the current air quality for a selected room 108. The flow rate of the air samples recovered from each room may be increased to limit the purge time, but such operation may require an air sample return device having increased power consumption, which may reduce operational efficiency and increase the noise of operation. Accordingly, the systems and methods disclosed provide for the air sampling system 100 to operate with improved efficiency while maintaining a responsive system having a short cycle time.

Figure 3:
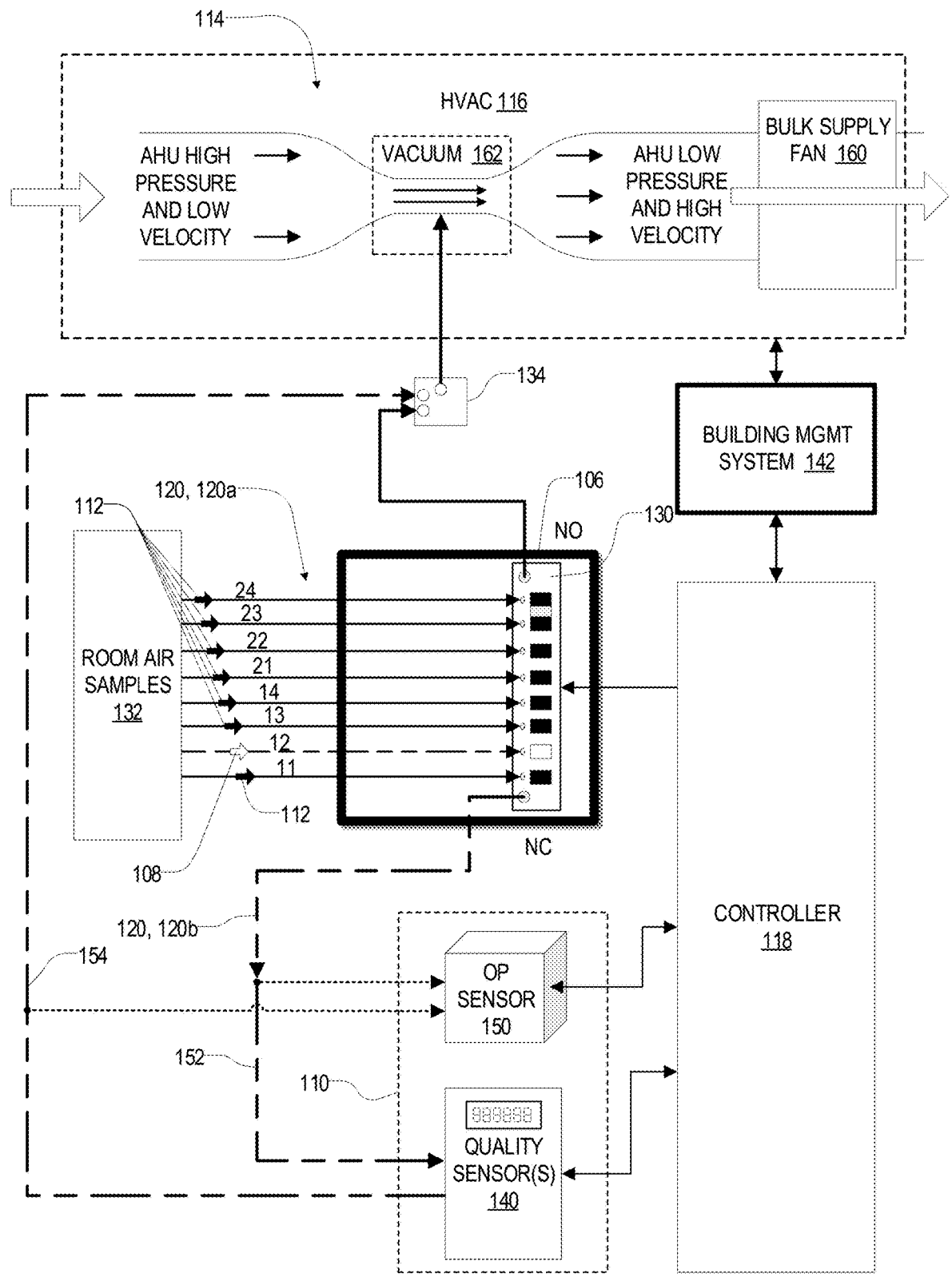
FIG. 3 is a schematic diagram of the air sampling system.

Referring now to FIG. 3, a schematic diagram of the air sampling system 100 is shown. As illustrated in FIG. 3, the air flow controller 106, the at least one sensor 110, and the sample return unit 114 are demonstrated in further detail. The air flow controller 106 may comprise a multi-input header 130 configured to receive each of a plurality of room air samples 132 from the plurality of rooms 102. The controller 118 may be configured to output a control signal to control the air flow controller 106 identifying a room of the plurality of rooms 102 to be measured for an air quality parameter or air condition. In response to receiving the signal, the air flow controller 106 may control one or more valves to direct the room air sample from the selected room 108 to the at least one sensor 110. In this way, the room air sample from the selected room 108 may be directed to the at least one sensor 110.

During operation, the room air samples 132 from each of the plurality of rooms 102 may be consistently delivered to the air flow controller 106 via the air sample supply lines 120a, each of which is in fluid communication with the air in one of the plurality of rooms 102. The room air samples 132 may be delivered at a rate of a volumetric displacement of air induced by a pressure differential generated in the sample return unit 114. The room air sample from the selected room 108 may be delivered to the at least one sensor 110. From the at least one sensor 110, the air may be drawn into the sample return unit 114 via a coupler 134. Concurrently to the delivery of the room air sample from the selected room 108, the room air samples from the idle rooms 112 may be drawn through the air flow controller 106 to the sample return unit 114 via the coupler 134. In this configuration, the room air samples 132 from each of the plurality of rooms 102 may be consistently delivered to the air flow controller 106 to provide updated room air samples for each of the plurality of rooms 102 throughout operation.

The at least one sensor 110 may correspond to a variety of types of sensors configured to measure one or more properties or air quality parameters of the room air samples 132. In some embodiments, the at least one sensor 110 may correspond to one or more air quality sensors 140 configured to detect a condition or change in condition in each of the room air samples 132. The air quality sensor 140 may be configured to communicate one or more measurements or other data to the controller 118. The controller 118 may process the one or more measurements or other data to identify air quality conditions or metrics for each of the plurality of rooms 102.

The measurements communicated to the controller 118 may be utilized to determine an appropriate action to improve the air quality for a specific room of the plurality of rooms 102. In this way, the controller 118 may identify a condition or change in condition in one or more air quality parameters. Based on the identified condition or change, the controller 118 may communicate a ventilation control signal configured to induce a building management system (BMS) 142 to take corrective action. In response to the ventilation control signal, the BMS 142 may control the HVAC system 116 to provide ventilation, heat, and/or cooled air to a specific room or group of rooms of the plurality of rooms 102.

In an exemplary embodiment, the air quality sensor 140 may correspond to a carbon dioxide ($CO_2$) sensor. The $CO_2$ sensor may be configured to measure a $CO_2$ level of the air in the selected room 108. In such an embodiment, the air quality sensor 140 (e.g. the $CO_2$ sensor) may be configured to communicate the $CO_2$ level of the selected room 108 to the controller 118. Based on a change or measurement of the $CO_2$ level, the controller 118 may communicate a ventilation control signal to the BMS 142. Based on the ventilation control signal, the BMS 142 may control the HVAC system 116 to provide ventilation, heating, or cooling to the selected room 108 (e.g. room 12). In this way, the system 100 may be configured to monitor the air quality of each of the rooms 102 and communicate the $CO_2$ level to the BMS 142. Accordingly, the system 100 may be utilized to determine if the ventilation supplied by the HVAC system 116 is sufficient to control the $CO_2$ level in each of the rooms and communicate the $CO_2$ level or a representative control signal to the BMS 142, such that the $CO_2$ level in each of the rooms 102 may be maintained by the building management system 142 within a desired operating range.

Throughout operation, the controller 118 may continue to inspect the room air samples from each of the rooms 102 by controlling the air flow controller 106 to cycle each of the plurality of rooms 102 as the selected room 108. For example, after the controller 118 has received the air quality parameter or measurement from the air quality sensor 140 for a first room (e.g. room 12), the controller 118 may output a signal configured to control the air flow controller 106 to deliver a room air sample from a second room (e.g. room 22) to the air quality sensor 140. The room air sample for the second room (e.g. room 22) may be measured by the air quality sensor 140, which may communicate an air quality parameter to the controller 118. Based on the air quality parameter from the second room (e.g. room 22), the controller 118 may communicate a ventilation control signal to the BMS 142. In response to the ventilation control signal, the BMS 142 may control a ventilation, heating, and/or cooling property of the air supplied to the second room (e.g. room 22). In this way, the air sampling device 104 may provide control information and/or measurement information configured to identify an air quality parameter of the each of the plurality of rooms 102.

Though discussed in reference to the $CO_2$ sensor, the air quality sensor 140 may correspond to any form of device configured to measure a condition or an air quality parameter of an air sample. For example, the air quality sensor 140 may correspond to one or more forms of volatile organic compound (VOC) sensors, humidity sensors, $CO_2$ sensors, carbon monoxide (CO) sensors, ozone sensors, etc. Accordingly, the air sampling device 104 may be configured to provide various forms of air quality information to the BMS 142. In various embodiments, the controller 118 of the air sampling device 104 may be configured to provide various signals, measurements, and/or control instructions to the building management system 142 to suit a particular application of the air sampling system 100.

The at least one sensor 110 of the system 100 may further comprise an operation sensor 150, which may correspond to an air flow rate sensor, differential pressure transmitter, pressure sensor, etc. The operation sensor 150 may be connected to an inlet line 152 and an outlet line 154 of the air quality sensor 140. In this configuration, the operation sensor 150 may be configured to identify if the air flow provided to the air quality sensor 140 is sufficient to measure the air quality parameter of the selected room 108. Additionally, the operation sensor 150 may be configured to identify a change in pressure over the operating life or maintenance cycle of the air sampling system 100. For example, the controller 118 may monitor pressure data supplied by the operation sensor 150 to identify a change in pressure over time or a pressure below a predetermined threshold. Such changes in operating pressure may be utilized by the controller 118 to identify a maintenance condition or failure in operation of the air sampling device 104.

Still referring to FIG. 3, the sample return unit 114 may correspond to an air transport motivator. The sample return unit 114 may correspond to an energy efficient air transport unit configured to function without a need for direct electrical power or a dedicated mechanical drive, vacuum or propulsion system. In such embodiments, the sample return unit 114 may be configured to generate suction to draw or transfer the room air samples 132 from each of the plurality of rooms 102 in response to being positioned within an air flow of a bulk supply fan 160 or air displacement device of the HVAC system 116. For example, the sample return unit 114 may correspond to a Venturi vacuum device configured to utilize differential pressure from the air flow in the form of a vacuum pump 162 derived from the bulk supply fan 160. The HVAC system 116 may be configured to provide heating, ventilation, and/or air conditioning to each of the rooms 102. In this configuration, the air sampling system 100 may be configured to function without a dedicated or air displacement device requiring energy that is not already utilized by operating the HVAC system 116.

Though the sample return unit 114 is described in the exemplary embodiment as a Venturi vacuum device, in some embodiments, the sample return unit 114 may recover the room air samples utilizing conventional vacuum pumps or fans. For example, in some embodiments, the sample return unit 114 may utilize suction created via a reciprocating pump, screw, or turbine compressor, or various devices configured to displace air in response to receiving electrical current. Such devices may be utilized to provide vacuum pressure to return the room air samples. However, these devices may be noisy, inefficient, and require more maintenance than the Venturi vacuum device disclosed herein.

As discussed herein in the exemplary embodiment, the only energy usage of the sample return unit 114 may be a small parasitic energy drawn from the bulk supply fan 160 of the HVAC system 116. For example, the bulk supply fan 160 may consume a small and potentially negligible increase in power to provide the suction necessary to operate the sample return unit 114. In this way, the air sampling system 100 may improve efficiency while limiting components and related maintenance that may be required when utilizing active devices to provide vacuum pressure to return the room air samples. Instead, the sample return unit 114 may utilize the existing fluid pressure from the HVAC system 116 to generate suction to power the sample return unit 114 via the Venturi effect to improve efficiency and limit maintenance.

In operation, the sample return unit 114 may draw room air samples from each of the plurality of rooms 102 perpetually during operation of the bulk supply fan 160 of the HVAC system 116. For example, the controller 118 of the air sampling system 100 may be configured to control the air flow controller 106 to direct a room air sample of a selected room 108 (e.g. room 12) to the air quality sensor 140. The air quality sensor 140 may then measure a condition or quality parameter of the selected room 108. Additionally, the air flow controller 106 may be configured to retrieve and purge room air samples 132 from each of the idle rooms 112 (e.g. rooms 11, 13, 14, and 21-24). By continuously drawing the room air samples 132 from each of the idle rooms 112 and the selected room 108, the air sampling system 100 may supply updated air samples to the air flow controller 106 without significant delay due to purging air samples. Accordingly, the air supplied to the at least one sensor 110 may only need to be purged of the air in the sensor supply line 120b when changing the selected room 108 among the plurality of rooms 102. In this way, the system may provide for economical monitoring of the air quality in each of the rooms 102 while maintaining a low cycle time for monitoring each of the rooms 102. Accordingly, the disclosure provides for a responsive monitoring system operable to quickly and effectively provide control information to the BMS 142 to ensure that room air quality is maintained throughout a building while limiting associated cost and maintenance fees.

Figure 4:
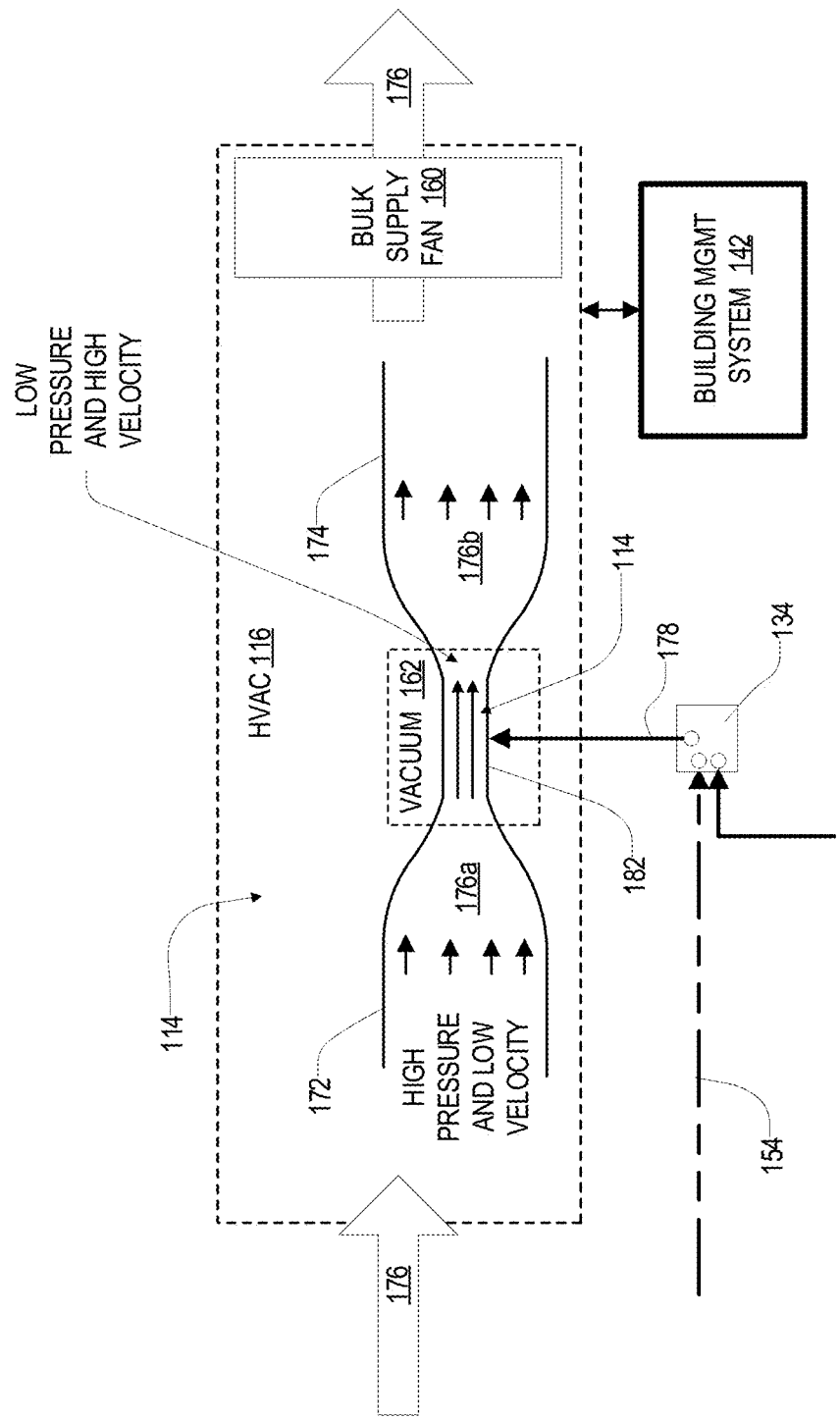
FIG. 4 is a detailed schematic diagram of the sample return unit of the air sampling system.

Referring to FIG. 4, a detailed schematic diagram sample return unit 114 of the air sampling device 104 is shown. As previously discussed, the sample return unit 114 may comprise the vacuum pump 162 configured to derive suction to draw or transfer the air samples from each of the plurality of rooms 102 to the air flow controller 106. The sample return unit 114 or air supply unit of the system 100 may be disposed in an air flow generated by an air supply unit or the bulk fan supply 160 of the HVAC system 116. The sample return unit 114 comprises an air inlet 172 and an air outlet 174. The air inlet 172 is configured to receive an inlet portion 176a of the air flow 176 and an outlet portion 176b released through the air outlet 174.

The inlet portion 176a of the air flow 176 may have an inlet pressure and an inlet velocity. The outlet portion 176b of the air flow 176 may have an outlet pressure and an outlet velocity. The sample return unit 114 may generate the suction of a suction line 178 by utilizing a pressure differential between the inlet pressure and a vacuum pressure in a vacuum section 182. For example, the pressure differential may be generated by the sample return unit 114 due to the Venturi effect causing the inlet pressure to be greater than a vacuum pressure in the vacuum section 182 between the inlet portion 176a and the outlet portion 176b. Additionally, the Venturi effect may cause the inlet velocity to be lower than an intermediate velocity between the inlet portion 176a and the outlet portion 176b. In this configuration, the difference between the inlet pressure and the vacuum pressure created by the sample return unit 114 generates the suction that draws the room air samples via the vacuum pump 162 between the air inlet 172 and the air outlet 174.

As previously discussed, the vacuum section 182 is disposed between the air inlet 172 and the air outlet 174. The vacuum section 182 forms a central cross-section perpendicular to the air flow 176. The central cross-section is smaller than an inlet cross-section of the air inlet 172 and an outlet cross-section of the air outlet 174. In this configuration, the changes in the cross-sections among the air inlet 172, the vacuum section 182, and the air outlet 174 may result in vacuum pressure to be generated at the connection between the suction line 178 and the vacuum section 182. In this configuration, the sample return unit 114 may draw the air samples from each of the plurality of rooms 102 to the air flow controller 106. Accordingly, the air samples may be drawn from the plurality of rooms 102 throughout the operation of the air sampling system 100 in response to the activation of the air flow generated by the bulk fan supply 160 of the HVAC system 116.

Figure 5:
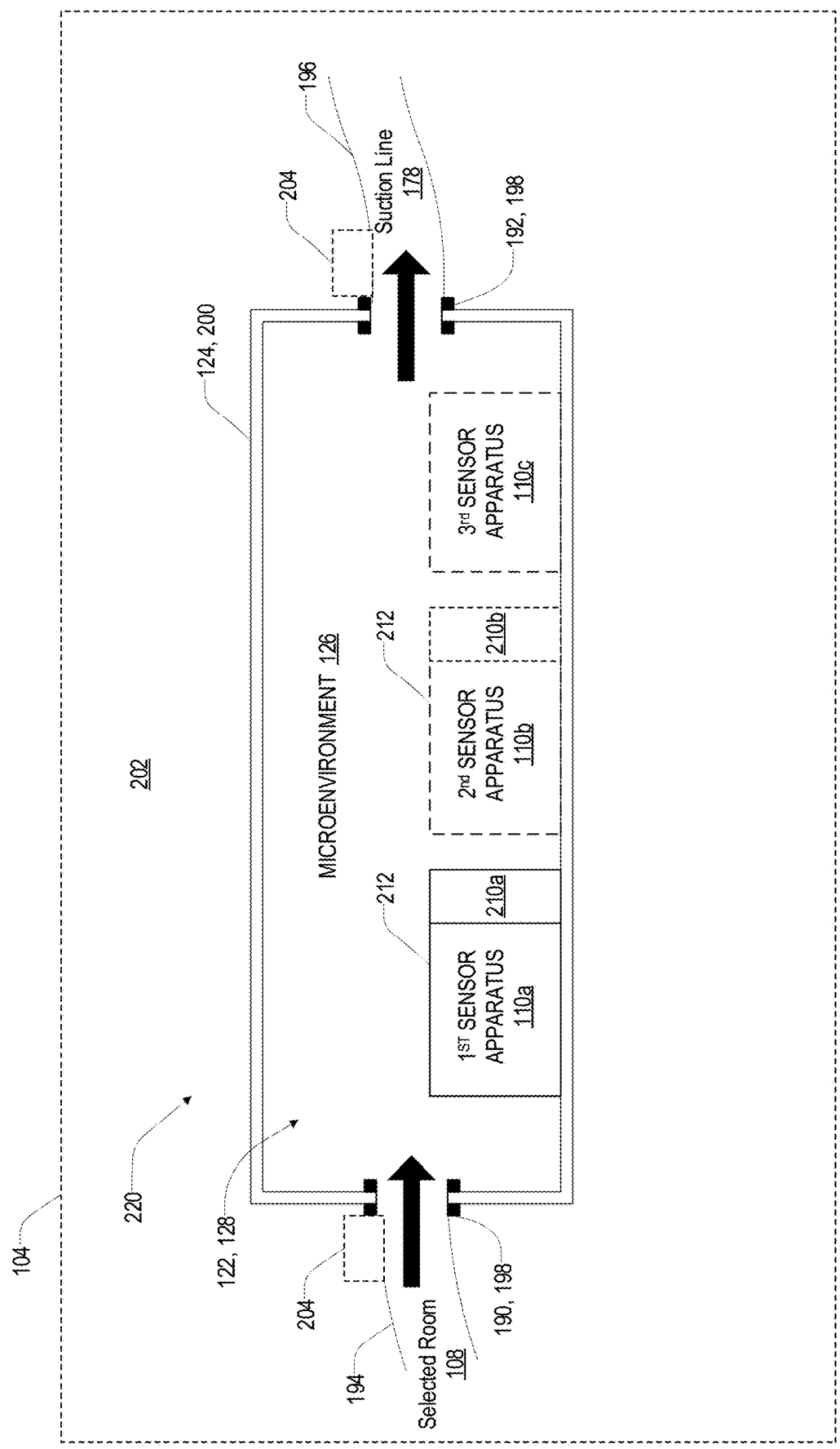
FIG. 5 is a cross-sectional diagram of a remote test apparatus configured to simulate ambient conditions of a room.
Figure 6:
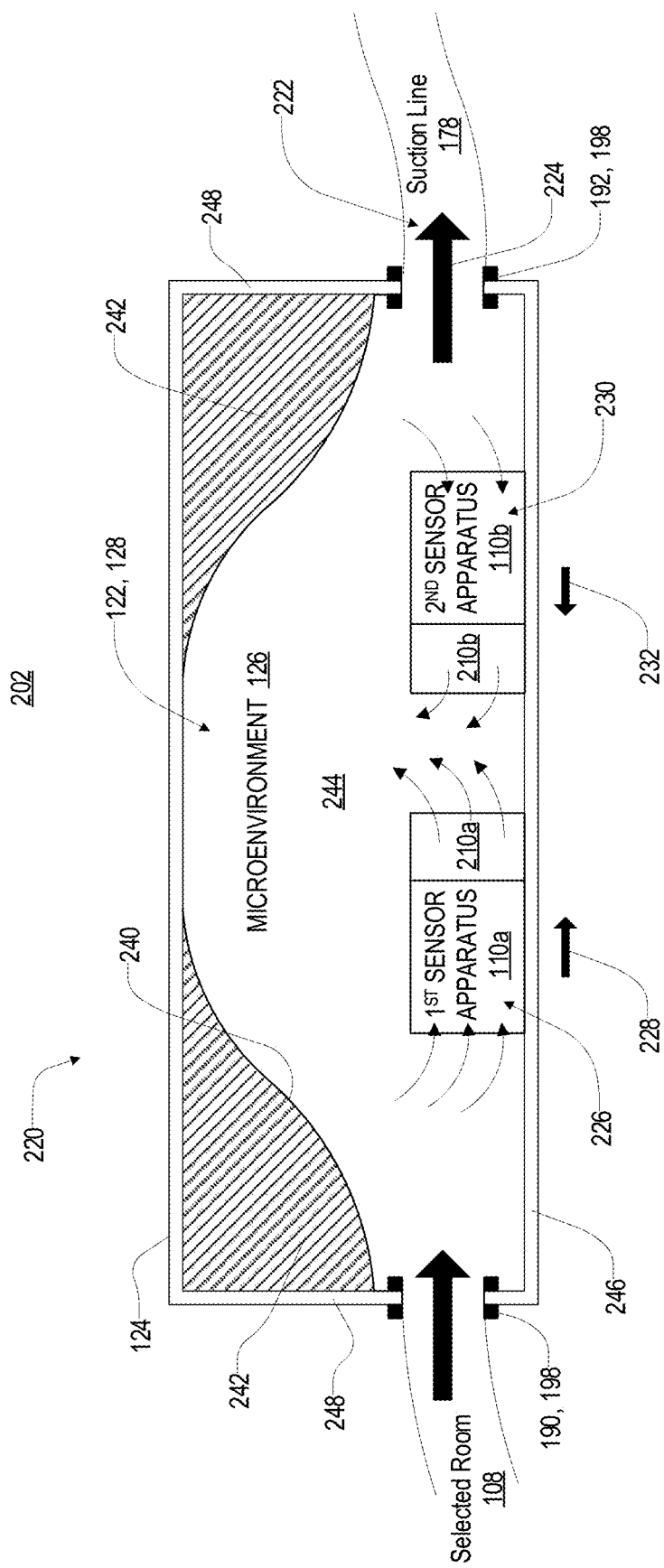
FIG. 6 is a side cross-sectional view of a remote test apparatus demonstrating a plurality of sensors in a micro-environment.
Figure 7:
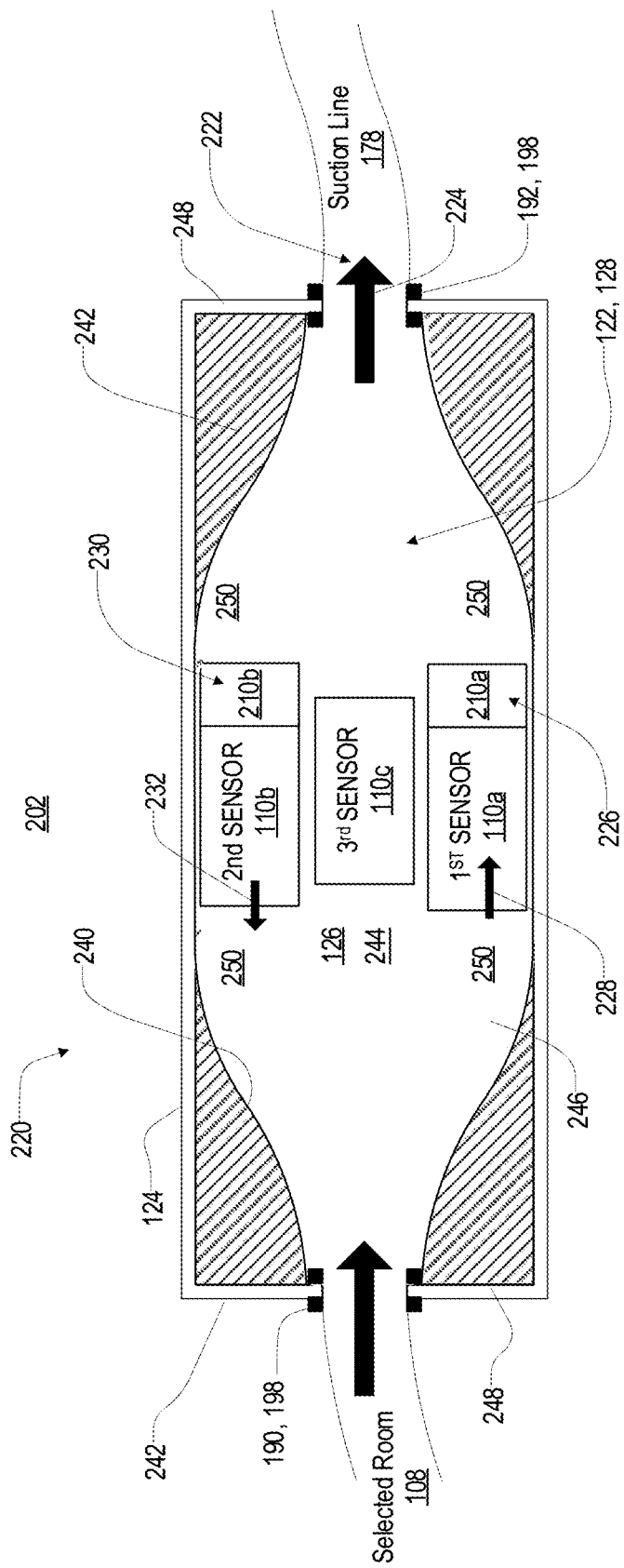
FIG. 7 is a top cross-sectional view of a remote test apparatus demonstrating a plurality of sensors in a micro-environment.

Referring now to FIGS. 5, 6, and 7; representative diagrams of the remote test environment 122 formed by the sealed enclosure 124 are shown demonstrating the operation of the remote test environment in coordination with the sampling device 104. As previously discussed, the remote test environment 122 is formed within the sealed enclosure 124, which may be housed within an enclosure of the sampling device 104. In operation, the air flow controller 106 may continuously cycle sampled air from each of the rooms 102 by drawing air from the rooms via the suction line 178. In order to test the selected room 108, the controller 106 may direct the air sample from the selected room 108 into the sealed enclosure 124, such that the micro-environment 126 is generated within the interior cavity 128 of the sealed enclosure 124. In this way, the system 100 may provide for a simulated environment with representative air quality conditions to that of the selected room 108 and each of the rooms 102 connected to the sampling device in a remote location separate from the rooms 102.

Within the remote test environment 122 formed by the sealed enclosure 124, at least one of the sensors 110 may be housed, such that the air flow controlled by the air flow controller 106 may be delivered from the selected room 108 into the interior cavity 128. In this way, the system may generate similar or representative ambient air conditions to those of the selected room 108 within the sealed enclosure 124, such that the one or more sensors 110 disposed therein may be operable to sample and test the micro-environment 126 and thereby simulate a test of the ambient air conditions within the selected room 108. The operation of the remote test environment 122 may be cycled for each of the rooms 102 in connection with the sampling device 104 without appreciable lag or delay as a result of the continuous delivery of the room air samples from each of the rooms 102. In this way, the system 100 may provide for advanced testing of simulated ambient air conditions in each of the rooms 102 while only requiring a limited vacuum pressure and corresponding flow rate of the room air samples supplied to the sampling device 104 by the flow controller 106.

As discussed herein each of the sensors 110 may correspond to an air quality or particulate air sensor, such as the air quality sensors 140 previously discussed herein. The air quality sensor 140 may correspond to any form of device configured to measure a condition or an air quality parameter of an air sample. For example, the air quality sensor 140 may correspond to one or more forms of volatile organic compound (VOC) sensors, humidity sensors, $CO_2$ sensors, carbon monoxide (CO) sensors, ozone sensors, flow rate sensors or flow meters, etc. Additionally, the air quality sensors may correspond to electro-chemical sensors that may be configured to detect one or more allergens or particulate materials suspended in the air within the selected room 108. Accordingly, the air sampling device 104 may be configured to provide various forms of air quality information to the BMS 142.

The sealed enclosure 124 of the remote test environment may be configured to receive the room air samples from the selected rooms 108 via an enclosure inlet 190. The air from the selected room 108 forming the micro-environment 126 may further be purged from the interior cavity 128 via the suction line 178. Inlet air supply line 194 may be connected to the enclosure inlet 190 via a sealed coupling 198. Similarly, an outlet purge line 196 may be coupled to enclosure outlet 192 via the sealed coupling 198. In this configuration, the air supply to the micro-environment 126 from the selected room 108 may be enclosed within a sealed boundary wall 200. In this configuration, the sample air within the remote test environment 122 may form the micro-environment 126 representative of the ambient air quality conditions within the selected room 108. The sealed boundary wall 200 may prevent seepage from a local environment 202 (e.g. the local environment of the sampling device 104) from entering the sealed enclosure 124 and interrupting or otherwise limiting accuracy of the representation of the air conditions within the micro-environment 126 relative to those in the selected room 108.

In operation, the sealed enclosure 124 and boundary wall 200 prevent contamination or seepage from the local environment from entering the interior cavity 128, which may otherwise adversely impact the accuracy of the test data captured by at least one sensor 110 disposed therein. Preventing seepage from the local environment may be of particular importance for the system 100 in implementations that utilize the sample return unit 114 in the form of a Venturi vacuum device for similarly low energy systems, which may derive differential pressure from air flow controllers for the HVAC system 116 of the building. For example, in systems that utilize sample return units 114 that are only operable to generate limited differential pressure (e.g. less than 2 inches of mercury or 70 mbar), seepage from the local environment 202 may form a significant portion of the air and related contaminates entering the micro-environment 126. Accordingly, in order to direct sufficient air from the selected room 108 into the micro-environment 126 via the suction line 178, the interior cavity 128 of the sealed enclosure 124 should be effectively sealed, particularly in systems that are optimized for efficient operation with limited flow rates passing through the interior cavity 128.

In some implementations, in order to insure the integrity of the sealed boundary wall 200 forming the interior cavity 128, the system 100 may further comprise a differential pressure sensor 204. The differential pressure sensor 204 may be in connection with or otherwise configured to detect the pressure between the enclosure inlet 190 and the enclosure outlet 192 in order to insure that the sealed boundary wall 200 has not been breached or otherwise compromised. Accordingly, the differential pressure sensor 204 may be in communication with the controller 118, such that the controller 118 may monitor pressure across the micro-environment 126 and thereby test the integrity of the sealed enclosure 124 and the sealed boundary wall 200. As demonstrated, the pressure sensor 204 is configured to detect an external pressure differential in order to ensure that the integrity of the boundary wall 200 and the connections (e.g., the inlet 190, outlet 192), and any external fittings are maintained such that the environment within the seal enclosure 124 is isolated from the environment outside the boundary wall 200. In this way, the system may diagnose potential leaks and various system operating defects in response to changes detected in the differential pressure.

As depicted in FIG. 5, the at least one sensor 110 may comprise a first sensor apparatus 110a, a second sensor apparatus 110b, and/or a third sensor apparatus 110c. Though three sensors are discussed in the exemplary implementation demonstrated in FIG. 5, it may be understood that additional sensors may be implemented without departing from the spirit of the disclosure. One or more of the sensors 110 may comprise an air transfer unit 210. Air transfer unit 210 may correspond to a fan, pump, or other air transfer devices that may be configured to electively communicate air within the micro-environment 126 and a housing or enclosure 212 of the one or more sensors 110. For example, the first sensor apparatus 110a may comprise a first air transfer unit 210a, and the second sensor apparatus 110b may comprise a second air transfer unit 210b. In this configuration, the controller 118 may control each of the first sensor apparatus 110a and the second sensor apparatus 110b to independently control the flow of the ambient air within the micro-environment 126 through their respective enclosures 212 in order to optimize operation of each of the sensors. One or more of the sensors 110, in the third exemplary sensor apparatus 110c, may be configured to operate in the localized conditions of the air within the micro-environment 126 without requiring a separate air transfer unit 210. Accordingly, the remote test environment 122 formed by the sealed enclosure 124 may provide for a remote test apparatus 220 that may be flexibly implemented to simulate and detect the ambient air conditions in each of the rooms 102.

In order to avoid interference among the sensors 110 in the micro-environment, the arrangement of the sensors 110 may be provided in a sequential order or along unique or otherwise non-overlapping flow paths within the micro-environment 126. For example, in the configuration shown in FIG. 5, the first sensor 110a may be a temperature sensor, the second sensor 110b may be a particulate air sensor, and the third sensor 110c may be a flowrate sensor or flow meter. More generally, in cases where a temperature sensor is included in the micro-environment, the temperature sensor may be arranged upstream from any sensors, particularly those that generate heat or otherwise could adjust a temperature of air supplied to the temperature sensor along the flow path identified by the arrows in inlet air supply line 194 and the suction line 178. In this arrangement, heat that may be introduced by the second or third sensors 110b, 110c is downstream of the air flow from the first sensor 110a, which preserves the accuracy of temperature readings by the first sensor 110a.

In addition to the first sensor 110a implemented as the temperature sensor positioned proximate to the inlet 190, the flow rate sensor may be positioned proximate to the outlet 192 similar to the third sensor 110c. Additionally, as discussed later in reference to FIG. 7, the first sensor 110a, the second sensor 110b, and/or the third sensor 110c may be arrange such that the flow of air within the micro-environment 126 does not result in the air interacting with the first sensor 110a being received by the second or third sensors 11b, 110c. More generally, the sensors in the micro-environment 126 or the sealed enclosure 124 may be arranged such that the directional flow of the air received at the inlet 190 and removed via the outlet 192 does not sequentially flow from one sensor 110 to another sensor 110 in cases where the sensors implemented may introduced heat, disrupt flow, or introduce other variables within the enclosure 124 that may affect the accuracy and response of the data collected by the sensors. Stated simply, the sensors 100 may be arranged such that fresh air samples are delivered to those sensors that are sensitive to variables that would be introduced in the wake of an upstream sensor.

Referring now to FIGS. 5 and 6, the first sensor apparatus 110a and the second sensor apparatus 110b are demonstrated in a first flow rate 222 generated by the differential pressure of the suction line 178 generated by the sample return unit 114. The first flow rate 222 may be drawn through the interior cavity 128 of the sealed enclosure 124 in a first direction 224, which may be substantially between the enclosure inlet 190 and the enclosure outlet 192. As previously discussed, each of the first sensor apparatus 110a and the second sensor apparatus 110b may be disposed within the micro-environment 126 formed by the enclosure 124, such that the sensors 110a, 110b may receive the air passing through the micro-environment 126 provided from the selected room 108 at the first flow rate 222. In this configuration, each of the sensors 110a, 110b may be configured to independently sample the simulated conditions from the selected room 108 within the micro-environment 126 by controlling their respective air transfer units 210a, 210b.

First sensor apparatus 110a may comprise the first air transfer unit 210a. The first air transfer unit 210a may be configured to draw air through the enclosure 212 at a second flow rate 226. Additionally, first air transfer unit 210a and enclosure 212 of the first sensor apparatus 110a may be oriented within the interior cavity 128, such that second flow rate 226 is directed in a second direction 228, which may be substantially aligned with the first direction 224 of the first flow rate 222. The second air transfer unit 210b within the enclosure 212 of the second transfer apparatus 110b is configured to draw or transfer the air from the micro-environment 126 through the enclosure 212 at a third flow rate 230. As depicted in FIG. 6, the air flow communicated by the second transfer unit 210b is directed in a third direction 232. The third direction 232 may be substantially opposite the first direction 224 of the flow controlled by the sample return unit 114. Accordingly, flow rate and direction of the sensors 110 may be independently controlled by the system 100 in order to provide for flexibility in operation.

As discussed herein, the directions 224, 228, and 232 of the respective flow rates 222, 226, and 230 are described as being substantially aligned or in substantial opposing directions. However, the directions 224, 228, and 232 of each of the flow rates 222, 226, and 230 may be arranged perpendicular, skewed, or in a variety of orientations relative to first direction 224 without departing from the spirit of the disclosure. As described herein, the term "substantially" in reference to the directions provides for variations in manufacturing, assembly, and time constraints of the interior cavity 128 micro-environment 126 that may result in alterations in the direction of the flow rates 222, 226, and 230 to various degrees. Accordingly, the term "substantially" may provide for variations of +/−10 degrees of alignment, which may provide for similar operating results while still maintaining the general relative directions described herein. Finally, while discussed in reference to the flow rates 222, 226, and 230, additional sensors 110 may include additional air transfer units 210 or may combine air transfer units in a variety of ways to independently control any number of flow rates for corresponding sensors that may be implemented within the constraints of the interior cavity 128.

Referring now to FIGS. 6 and 7, the interior cavity 128 of the sealed enclosure 124 may comprise one or more contoured walls 240 formed by partitions 242 of sealed enclosure 124 or may be formed from the same mold as the sealed enclosure 124. In general, the contoured interior walls 240 may provide for contoured shape of the micro-environment 126 approximate the enclosure inlet 190 and enclosure outlet 192. In this configuration, sealed enclosure 124 may provide for an expanded central region 244 enclosed between the enclosure inlet 190 and the enclosure outlet 192. The expanded central region 244 may provide for a volume of air from the selected room 108 to be housed within the enclosure 124, such that the one or more sensors 110 enclosed within interior cavity 128 have ample air within the micro-environment 126 to effectively simulate the selected room 108. The proportions of the interior cavity 128 and the expanded central region 244 may be dependent upon the particular type of operating environments for each of the sensors 110. Accordingly, the proportions of the micro-environment 126 may be adjusted or varied to suit a variety of applications based on the teachings of the disclosure.

As depicted in FIG. 6, contoured interior walls 240 are demonstrated in reference to a side cross-sectional view of the cavity 128. As shown, the sensors 110 may be disposed along a base 246 of the sealed enclosure 124 which may extend proximate to enclosure inlet 190 and enclosure outlet 192. In this configuration, the air supply lines 194, 196 may pass through the side walls 248 of the sealed enclosure 124, such that the enclosure inlet 190 and enclosure outlet 192 are proximate to the base 246. In this configuration, the first flow rate 222 flows through the interior cavity 128 via the suction line 178 may be aligned with the sensors 110 disposed along the base 246 of the sealed enclosure 124 within the interior cavity 128.

As demonstrated in FIG. 7, a top cross-sectional view of the interior cavity 128 demonstrates walls 240 opening to the expanded central region 244, enclosure inlet 190 and enclosure outlet 192. As shown, the sensors 110 range such that air communicated form the selected room 108 to the suction line 178 is directed across the enclosures 212 of each of the sensors 110. Additionally, the first sensor apparatus 110a and the second sensor apparatus 110b are arranged along the contoured interior walls 240, while the third sensor apparatus 110c is disposed centrally within the expanded central region 244 formed by the interior cavity 128. The arrangement demonstrated in FIG. 7 may be beneficial in that the transfer units 210 of the first sensor apparatus 110a and the second sensor apparatus 110b may communicate the air through the sensor enclosures 212, such that their position in the interior cavity 128 is less critical than that of the third sensor apparatus 110c, which is depicted without the air transfer unit 210. Such an arrangement may be beneficial in circumstances where the specific proportions or limitations of the first flow rate create limited flow zones 250 along the contoured interior walls 240. Accordingly, first and second air transfer units 210a, 210b may circulate the air through the enclosures 212 of the first sensor apparatus 110a and the second sensor apparatus 110b to improve the circulation of the air through the limited flow zones formed within the interior cavity 128. In this way, the operation of the system 100 may be optimized based on the particular sensors implemented therein.

As previously discussed, one or more of the sensors 100 may be arranged within the micro-environment 126 such that fresh air samples are delivered to those sensors that are sensitive to variables that would be introduced in the wake of an upstream sensor. As demonstrated in FIG. 7, the first sensor 110a, the second sensor 110b, and/or the third sensor 110c may be arrange such that the flow of air within the micro-environment 126 does not result in the air interacting with the first sensor 110a being received by the second or third sensors 110b, 110c. This may be particularly important in cases where the first sensor 110a is a temperature sensor could be detect heat emitted from an upstream sensor if not arranged to receive air freshly supplied from the inlet 190. More generally, the sensors in the micro-environment 126 or the sealed enclosure 124 may be arranged such that the directional flow of the air received at the inlet 190 and removed via the outlet 192 does not sequentially flow from one sensor 110 to another sensor 110 in cases where the sensors implemented may introduced heat, disrupt flow, or introduce other variables within the enclosure 124 that may affect the accuracy and response of the data collected by the sensors.

Figure 8:
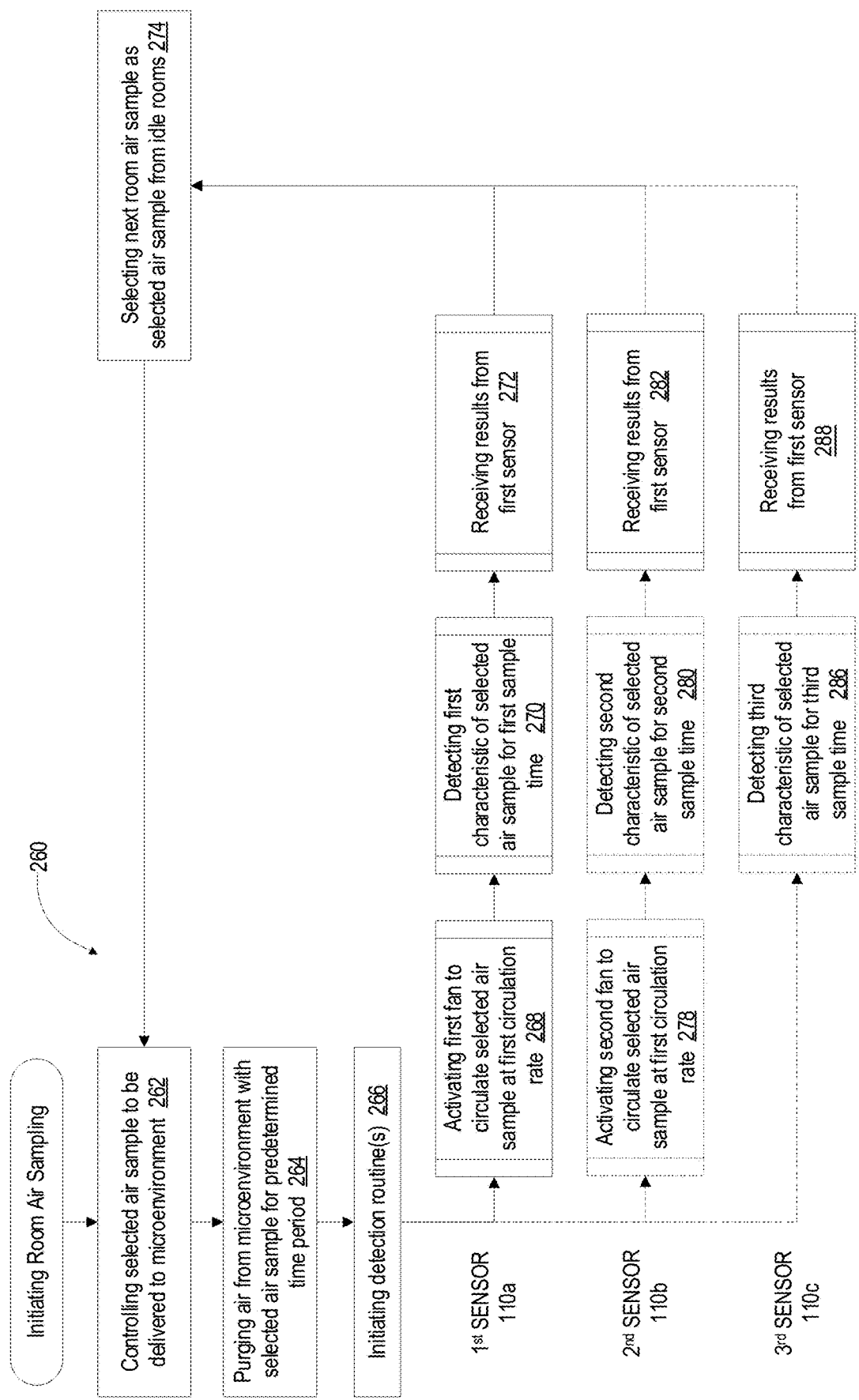
FIG. 8 is a flow chart demonstrating a method for controlling a remote test apparatus to detect simulated environmental conditions for a room in connection with an air sampling system in accordance with the disclosure.

Referring now to FIG. 8, a flow chart is shown demonstrating an exemplary operation of the system 100 comprising the remote test apparatus 220. The method 260 may begin by initiating operation for rooms 102 of the building 10. The operation may be initiated by the controller 118 controlling the sample return unit 114 to select the air sample from the selected room 108 to be delivered to the micro-environment 126 (262). Once initiated, the air supplied to the micro-environment 126 from the selected room 108 may be purged from the interior cavity 128 out through the suction line 178 for a predetermined time period (264). Once the air within the micro-environment 126 is purged over the predetermined time period, the air within the interior cavity 128 is representative of the ambient air conditions of the selected room 108. Once the micro-environment 126 is representative of the selected room, the method 260 may continue by initiating detection routines for one or more sensors 110 (266).

With reference to the first sensor apparatus 110a, the controller 118 may activate the first air transfer unit 210a to circulate the air from the micro-environment 126 through the enclosure 212 at the first flow or circulation rate (268). Following the activation of the first air transfer unit 210a, the controller may command the sensor within the first sensor apparatus 110a to detect a first or multiple characteristics of the air sample from the micro-environment 126 (270). Once the results are captured by the first sensor apparatus 110a, controller 118 may monitor and receive results from the first sensor apparatus 110a and report them or otherwise utilize the results to report the air quality and/or control the building management system 142 (272). Following step 272, the controller 118 may control the sampling device 104 to select the next room in sequence as the selected room 108 of the rooms 102 and return to step 262 (274).

In reference to the second sensor apparatus 110b, controller 118 may activate the second air transfer unit 210b to circulate the air from the micro-environment 126 through the enclosure 212 at the second flow or circulation rate (278). Following the activation of the second air transfer unit 210b, the controller may command the sensor within the second sensor apparatus 110b to detect a first or multiple characteristics of the air sample from the micro-environment 126 (280). Once the results are captured by the second sensor apparatus 110b, controller 118 may monitor and receive results from the second sensor apparatus 110b and report them or otherwise utilize the results to report the air quality and/or control the BMS 142 (282). Following step 282, the controller 118 may control the sampling device 104 to select the next room in sequence as the selected room 108 of the rooms 102 and return to step 262 (274).

Similar to the first sensor apparatus 110a and the second sensor apparatus 110b, the controller may activate the third sensor apparatus 110c to detect one or more quality factors or metrics related to forming the micro-environment 126 from the selected room 108 (286). The results from the third sensor apparatus 110c may be communicated to the controller 118 in accordance with the disclosure (288). Following step 284, the method 260 may return to step 274 as previously discussed. Accordingly, the system 100 may be configured to simultaneously control the operation of the first sensor apparatus 110a, the second sensor apparatus 110b, and the third sensor apparatus 110c to monitor the micro-environment 126. In this way, the controller 118 may detect the quality metrics identified by each of the sensors 110 in parallel or over a combined, overlapping temporal period within the single micro-environment 126.

Additionally, as the conditions within the micro-environment 126 are representative of the ambient conditions within the selected room 108, the controller 118 may apply a comparative analysis to the information communicated from one or more of the sensors 110. The comparison of the results by the controller 118 from the sensors 110 may be utilized to identify a fault or cross-reference results between or among the quality metrics identified by the sensors 110. In this configuration, the micro-environment 126 and corresponding sensors 110 may provide comparative information for the conditions within the micro-environment 126, which may be utilized for troubleshooting, sensor redundancy, and/or determinations of the validity of the results communicated from the sensors 110. Accordingly, the utilization of the micro-environment 126 may provide for various benefits to improve the reliability, performance, and capability of the system 100.

It will be appreciated that embodiments of the disclosure described herein may be comprised of one or more conventional processors and unique stored program instructions that control one or more processors to implement, in conjunction with certain non-processor circuits, some, most, or all of the functions of an image sensor system and method thereof, as described herein. The non-processor circuits may include, but are not limited to, signal drivers, clock circuits, power source circuits, and/or user input devices. Alternatively, some or all functions could be implemented by a state machine that has no stored program instructions, or in one or more application specific integrated circuits (ASICs), in which each function or some combinations of the functions are implemented as custom logic. Of course, a combination of the two approaches could be used. Thus, the methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

It should be appreciated by those skilled in the art that the above described components may be combined in additional or alternative ways not explicitly described herein. Modifications of the various implementations of the disclosure will occur to those skilled in the art and to those who apply the teachings of the disclosure. Therefore, it is understood that the embodiments shown in the drawings and described above are merely for illustrative purposes and not intended to limit the scope of the disclosure, which is defined by the following claims as interpreted according to the principles of patent law, including the Doctrine of Equivalents.

What is claimed is:

1. A remote test apparatus configured to monitor an environment of at least one remotely located room and configured to receive at least one air sample from the at least one remotely located room, the apparatus comprising:
    a sealed enclosure forming an interior cavity and comprising an inlet in connection with the at least one remotely located room and an outlet in connection with a sample collection unit, wherein the sample collection unit is configured to communicate the at least one air sample from the remotely located room at a first flow rate;
    at least one sensor disposed in a housing in fluid communication with the interior cavity; and
    at least one air transfer unit configured to transfer test air from the interior cavity of the sealed enclosure to the housing of the sensor at a second flow rate different from the first flow rate.

2. The remote test apparatus according to claim 1, wherein the at least one sensor comprises a first sensor and a second sensor.

3. The remote test apparatus according to claim 2, wherein the at least one air transfer unit comprises a first air transfer unit configured to transfer the test air from the interior cavity of the sealed enclosure to the first sensor at the second flow rate.

4. The remote test apparatus according to claim 3, wherein the at least one air transfer unit comprises a second air transfer unit configured to transfer the test air from the interior cavity of the sealed enclosure to the second sensor at the third flow rate.

5. The remote test apparatus according to claim 4, wherein the second flow rate is different than the third flow rate.

6. The remote test apparatus according to claim 4, further comprising:
    a controller, wherein the controller is configured to detect a first air quality condition via the first sensor and a second air quality condition via the second sensor.

7. The remote test apparatus according to claim 6, wherein the controller is configured to independently control a first test cycle time of the first sensor and a second test cycle time of the second sensor over a test period.

8. The remote test apparatus according to claim 7, where the first test cycle time and the second test cycle time overlap within the test period.

9. The remote test apparatus according to claim 1, wherein the at least one sensor is disposed in a sensor enclosure in connection with the at least one air transfer unit, wherein the at least one air transfer unit is configured to supply the test air from the interior cavity to the at least one sensor at the second flow rate, wherein the sample collection unit is configured to communicate the at least one air sample from the remotely located room at the first flow rate in a first direction extending from the inlet to the outlet.

10. The remote test apparatus according to claim 9, wherein the at least one air transfer unit is configured to transfer the test air through the enclosure in a second direction different than the first direction.

11. The remote test apparatus according to claim 1, further comprising:
    a pressure sensor configured to detect a pressure differential between the interior cavity and a local environment proximate the sealed enclosure; and
    a controller configured to detect a system error in response to changes in the pressure differential.

12. The remote test apparatus according to claim 1, wherein the housing at least partially partitions the sensor from the interior cavity and the test air is transferred to the sensor in the housing by at least one of a fan or pump.

13. A method for monitoring an environmental condition of at least one remotely located room, the method comprising:
    supplying at least one air sample at a first flow rate from the at least one remotely located room to an interior cavity of a sealed enclosure;
    transferring a portion of the at least one air sample from within the interior cavity to a second sensor in communication with interior cavity with an air transfer device at a second flow rate different than the first flow rate; and
    detecting the environmental condition of the portion of the at least one air sample at the second flow rate, wherein a test environment within the interior cavity generates the environmental condition representative of the remotely located room.

14. The method according to claim 13, wherein the portion of the at least one air sample is actively transferred through an enclosure housing the second sensor.

15. A remote test apparatus configured to monitor an environment of at least one remotely located room and configured to receive at least one air sample from the at least one remotely located room, the apparatus comprising:
    a sealed enclosure forming an interior cavity formed by a sealed boundary wall, the sealed enclosure comprising an inlet in connection with the at least one remotely located room and an outlet in connection with a sample collection unit, wherein the at least one sample collection unit is configured to communicate the at least one air sample from the remotely located room at a first flow rate; and at least one sensor disposed in a sensor enclosure in the interior cavity; wherein the at least one sample collection unit is configured to supply a portion of the at least one air sample to the sensor enclosure at a second flow rate different from the first flow rate.

16. The remote test apparatus according to claim 15, further comprising: a pressure sensor configured to detect a pressure differential within the sealed enclosure derived from the operation of the sample collection unit; and a controller configured to detect an operational error in response to changes in the pressure differential, wherein the operational error indicates a leak in the sealed boundary wall allowing air from the local environment to enter the sealed enclosure.

17. The remote test apparatus according to claim 15, wherein the at least one air sample at the first flow rate passes along a flow path directionally extending from the inlet to the outlet and the at least one sensor comprises a first sensor and a second sensor.

18. The remote test apparatus according to claim 17, wherein the first sensor is a temperature sensor and the first sensor is arranged upstream along the flow path from the second sensor.

19. The remote test apparatus according to claim 18, wherein the temperature sensor positioned proximate the inlet and the second sensor generates heat in operation.

* * * * *